United States Patent
Patel et al.

(10) Patent No.: US 11,648,207 B1
(45) Date of Patent: May 16, 2023

(54) EXTENDED RELEASE PHARMACEUTICAL COMPOSITION OF CLOZAPINE

(71) Applicant: Intas Pharmaceuticals Ltd., Ahmedabad (IN)

(72) Inventors: Rikin Patel, Ahmedabad (IN); Kavan Pandya, Ahmedabad (IN); Piyush Kansagra, Ahmedabad (IN); Satyavan Dhavale, Ahmedabad (IN); Ashish Sehgal, Ahmedabad (IN)

(73) Assignee: Intas Pharmaceuticals Ltd.

( * ) Notice: Subject to any disclaimer, the term of this patent is extended or adjusted under 35 U.S.C. 154(b) by 0 days.

(21) Appl. No.: 17/716,790

(22) Filed: Apr. 8, 2022

(30) Foreign Application Priority Data

Dec. 15, 2021 (IN) .............................. 202121058300

(51) Int. Cl.
| | |
|---|---|
| *A61K 9/51* | (2006.01) |
| *A61K 9/50* | (2006.01) |
| *A61K 31/5513* | (2006.01) |
| *A61K 9/00* | (2006.01) |

(52) U.S. Cl.
CPC ........ *A61K 9/5084* (2013.01); *A61K 31/5513* (2013.01); *A61K 9/0053* (2013.01)

(58) Field of Classification Search
None
See application file for complete search history.

(56) References Cited

U.S. PATENT DOCUMENTS

| | | | | |
|---|---|---|---|---|
| 2005/0163858 | A1* | 7/2005 | Boehm | A61K 9/2027 514/259.41 |
| 2008/0069878 | A1* | 3/2008 | Venkatesh | A61K 9/5026 514/355 |
| 2008/0175903 | A1* | 7/2008 | Hopkins | A61P 25/00 514/249 |

FOREIGN PATENT DOCUMENTS

| | | | |
|---|---|---|---|
| RU | 2414903 C1 | 10/2009 | |
| WO | 2006059194 A2 | 6/2006 | |
| WO | WO-2010096820 A1 * | 8/2010 | ........... A61K 9/0056 |
| WO | 2017142438 A1 | 8/2017 | |
| WO | 2018051292 A1 | 3/2018 | |
| WO | WO-2018051292 A1 * | 3/2018 | ......... A61K 31/5513 |

* cited by examiner

*Primary Examiner* — Susan T Tran
(74) *Attorney, Agent, or Firm* — McAndrews, Held & Malloy, Ltd.

(57) ABSTRACT

Disclosed is an extended release pharmaceutical composition of Clozapine, which can be provided as a reservoir type dosage form, and when dosed to a patient once daily achieves at steady state, $AUC_{0-24h}$, $C_{max}$ and $C_{min}$ in patient plasma that are within 80 to 125% bioequivalence criteria compared to immediate release Clozapine dosed at the same total daily dose divided twice per day. Further, the pharmaceutical composition of Clozapine can provide once daily dosing regimen in order to improve patient compliance and reduces side effects in patients in need thereof. The pharmaceutical composition further lacks any significant food effect on oral administration.

11 Claims, No Drawings

EXTENDED RELEASE PHARMACEUTICAL COMPOSITION OF CLOZAPINE

RELATED APPLICATIONS

This application is related to and claims priority to Indian Patent Application No. 202121058300, filed Dec. 15, 2021, which is incorporated by reference herein in its entirety.

FIELD OF THE INVENTION

The disclosure provides an extended release pharmaceutical composition of Clozapine, wherein the pharmaceutical composition is a reservoir type dosage form, and when dosed to a patient once daily achieves at steady state, $AUC_{0-24h}$, $C_{max}$ and $C_{min}$ in the patient's plasma that are within 80 to 125% bioequivalence criteria compared to immediate release Clozapine dosed at the same total daily dose divided twice per day. Further, the pharmaceutical composition of Clozapine provides once daily dosing regimen in order to improve patient compliance and reduces side effects in patients in need thereof. Furthermore, the pharmaceutical composition of Clozapine lacks a significant food effect on oral administration.

BACKGROUND

Clozapine is classified as an "atypical" antipsychotic drug. The chemical name for Clozapine is 8-chloro-11-(4-methyl-1-piperazinyl)-5H-dibenzo[b,e][1,4]diazepine with the following structure (Formula I):

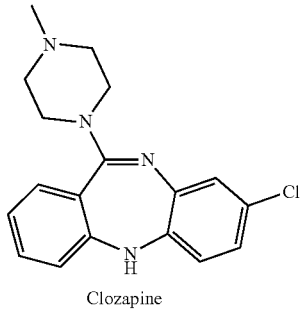

(Formula I)

Clozapine

Clozapine is a yellow, crystalline powder, very slightly soluble in water. The molecular formula is $C_{18}H_{19}ClN_4$ and the molecular weight is 326.83.

Clozapine is used for the management of severely ill schizophrenic patients who fail to respond adequately to standard drug treatment for schizophrenia. Clozapine is also used for reducing the risk of recurrent suicidal behavior in patients with schizophrenia or schizoaffective disorder who are judged to be at chronic risk for re-experiencing suicidal behavior, based on history and recent clinical state. Clozapine is also used in the treatment of Parkinson related psychosis.

Clozapine was first disclosed in U.S. Pat. No. 3,539,573 and is classified as an atypical anti-psychotic agent. Clozapine is marketed by Novartis in the US as CLOZARIL® immediate release tablets.

The mean terminal half-life of Clozapine is 12 hours, so multiple dosing is required to maintain steady state. The half-life of Clozapine causes peaks and fluctuations in its blood concentration, which leads to problems associated with toxicity and patient compliance due to multiple dosing requirements that can be necessary to maintain steady state levels. Thus, there is a need to provide alternative Clozapine compositions and dosage forms that can increase the therapeutic efficacy, reduce the fluctuations in drug concentration in the blood, and improve patient compliance.

SUMMARY

The object of the present invention is to provide an extended release pharmaceutical composition of Clozapine, wherein the pharmaceutical composition is a reservoir type dosage form, and when dosed to a patient once daily achieves at steady state, $AUC_{0-24h}$, $C_{max}$ and $C_{min}$ in the patient's plasma that are within 80 to 125% bioequivalence criteria compared to immediate release Clozapine dosed at the same total daily dose divided twice per day.

Another object of the present invention is to provide a method for maintaining a therapeutically effective concentration of Clozapine to improve patient compliance, reduce side effect and reduce patient burden to take multiple pills, wherein the method comprises administering to the patient, 12.5 mg to 400 mg of Clozapine in the extended release pharmaceutical composition.

Another object of the present invention is to provide an extended release pharmaceutical composition of Clozapine, wherein the pharmaceutical composition is in the form of granules, pellets, beads or spheroids, and the pharmaceutical composition is dispensed or compressed in the form of tablets or mini-tablets, or filled in capsules to provide pharmaceutical composition of Clozapine for oral administration.

Another object of the present invention is to provide an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day.

Another object of the present invention is to provide an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits following pharmacokinetic characteristic: a minimum drug concentration in plasma at steady state ($C_{min}$) from 20 ng/ml to 1070 ng/ml.

Another object of the present invention is to provide an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits following pharmacokinetic characteristic: a maximum drug concentration in plasma at steady state ($C_{max}$) from 130 ng/ml to 2280 ng/ml.

Another object of the present invention is to provide an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits following pharmacokinetic characteristic: an area under the time/plasma concentration curve from time 0 to 24 hours at steady state ($AUC_{0-24h}$) from 2130 ng/ml to 35630 ng/ml.

Another object of the present invention is to provide an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits following pharmacokinetic characteristic: a minimum drug concentration in plasma at steady state ($C_{min}$) of from 20 ng/ml to 1070 ng/ml, a maximum drug concentration in plasma at steady state ($C_{max}$) of from 130 ng/ml to 2280 ng/ml, an area under the time/plasma concentration curve from time 0 to 24 hours at steady state ($AUC_{0-24h}$) from 2130 ng/ml to 35630 ng/ml.

Another object of the present invention is to provide an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits following pharmacokinetic characteristic: average minimum drug concentration in plasma at steady state ($C_{min-avg}$) is of about 150 ng/ml to 400 ng/ml for a mean duration of about 24 hours.

Another object of the present invention is to provide an extended release pharmaceutical composition of Clozapine, wherein the pharmaceutical composition is a reservoir type dosage form containing 200 mg of Clozapine, and when dosed to a schizophrenic patient once daily, achieves at steady state, an $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits following pharmacokinetic characteristic: average maximum drug concentration in plasma at steady state ($C_{max-avg}$) is of about 550 ng/ml to 750 ng/ml for a mean duration of about 24 hours.

Another object of the present invention is to provide an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits following pharmacokinetic characteristic: average area under the time/plasma concentration curve at steady state from time 0 to 24 hours ($AUC_{0-24h,avg}$) is of about 8000 to 12000 ng·h/ml.

Another object of the present invention is to provide an extended release pharmaceutical composition of Clozapine, wherein the pharmaceutical composition lacks a significant food effect on oral administration.

Other aspects and embodiments will be apparent to those of skill in the art upon review of the following detailed description.

DETAILED DESCRIPTION

The extended release pharmaceutical composition disclosed herein advantageously provides for comparable, the same, or better in vivo bioavailability relative to the intake of commercially existing CLOZARIL® immediate release tablets, at equivalent doses of Clozapine extended release composition of 12.5 mg to 400 mg once daily. The inventors have generated Clozapine extended release capsules that can be administered once daily and provide a total drug exposure that is bioequivalent to the total drug exposure obtained after the twice daily administration of CLOZARIL® immediate release tablets.

As discussed in more detail below, the disclosure relates to an extended release pharmaceutical composition of Clozapine, wherein the pharmaceutical composition is a reservoir type dosage form, and when dosed to a patient once daily achieves at steady state, $AUC_{0-24h}$, $C_{max}$ and $C_{min}$ in the patient's plasma that are within 80 to 125% bioequivalence criteria compared to immediate release Clozapine dosed at the same total daily dose divided twice per day. Further, the pharmaceutical composition of Clozapine according to the present invention provides once daily dosing regimen to improve patient compliance, reduce side effects and lacks significant food effect on oral administration.

The food effect can have a significant impact during the development of a drug. In some cases, the food-drug interactions lead to an increase of drug absorption and the drug formulation may be recommended to be taken with food in order to be sufficiently absorbed and exert its expected clinical effect. In certain cases, food effect reduces $C_{max}$ and $T_{max}$ leading to significant change in the rate of drug absorption. In some instances where there exists a food effect on the drug absorption, warnings may be provided to the user to take the drug at specific timings, for example, one hour before or two hours after eating.

The compositions disclosed herein comprising 12.5 mg to 400 mg of Clozapine as once daily treatment represents significant improvement over other Clozapine compositions and formulations, including commercially available Clozapine immediate release tablets. The present invention provides a patient-friendly solution for an unmet medical need, better patient compliance, and lacks any significant food effect on oral administration.

However, none of the prior art teaches about how the reservoir type dosage form of the present invention provides comparable pharmacokinetic parameters on bioavailability with immediate release tablets administered twice daily to a patient in need thereof.

Although some attempts to prepare an extended release dosage form of Clozapine have been described, those attempts have demonstrated the difficulty in developing an extended release composition of Clozapine with an acceptable or desirable pharmacokinetic profile. This is apparent from the fact that currently there are no commercially available dosage forms of Clozapine extended release composition.

Accordingly, the disclosure addresses a long-felt need for an extended release pharmaceutical composition of Clozapine such as, for example, a reservoir type dosage form, that when administered once daily achieves at steady state $AUC_{0-24h}$, $C_{max}$ and $C_{min}$ in plasma within 80 to 125% bioequivalence criteria when compared to twice-daily immediate release Clozapine at the same total daily dose. The extended release composition of the present invention provides 12.5 mg to 400 mg Clozapine as once daily treatment, thereby reducing the patient pill burden, reducing toxicity and also improves patient compliance.

In a first embodiment, the present invention relates to an extended release pharmaceutical composition of Clozapine, wherein the pharmaceutical composition is a reservoir type dosage form, and when dosed to a patient once daily achieves at steady state, $AUC_{0-24h}$, $C_{max}$ and $C_{min}$ in the patient's plasma that are within 80 to 125% bioequivalence criteria compared to immediate release Clozapine dosed at the same total daily dose divided twice per day.

In another embodiment, the present invention relates to provide an extended release pharmaceutical composition of Clozapine, wherein the pharmaceutical composition is a reservoir type dosage form, and when dosed to a patient once daily achieves at steady state, $AUC_{0-24h}$, $C_{max}$ and $C_{min}$ in the patient's plasma that are within 80 to 125% bioequivalence criteria compared to immediate release Clozapine dosed at the same total daily dose divided twice per day.

In another embodiment, the present invention relates to provide a method for maintaining a therapeutically effective concentration of Clozapine to improve patient compliance, reduce side effect and reduce patient burden to take multiple pills, wherein the method comprises administering to the patient, 12.5 mg to 400 mg of Clozapine in an extended release pharmaceutical composition.

In another embodiment, the present invention relates to provide an extended release pharmaceutical composition of Clozapine, wherein the pharmaceutical composition is in the form of granules, pellets, beads or spheroids, and the pharmaceutical composition is dispensed or compressed in the form of tablets or mini-tablets, or filled in capsules to provide pharmaceutical composition of Clozapine for oral administration.

In another embodiment, the present invention relates to provide an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day.

In another embodiment, the present invention relates to provide an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits the pharmacokinetic characteristic of a minimum drug concentration in plasma at steady state ($C_{min}$) 20 ng/ml to 1070 ng/ml.

In another embodiment, the present invention relates to provide an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits the pharmacokinetic characteristic of a maximum drug concentration in plasma at steady state ($C_{max}$) from 130 ng/ml to 2280 ng/ml.

In another embodiment, the present invention relates to provide an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits the pharmacokinetic characteristic of an area under the time/plasma concentration curve from time 0 to 24 hours ($AUC_{0-24h}$) from 2130 ng/ml to 35630 ng/ml.

In another embodiment, the present invention relates to provide an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits the pharmacokinetic characteristic of: a minimum drug concentration in plasma ($C_{min}$) of from 20 ng/ml to 1070 ng/ml, a maximum drug concentration in plasma ($C_{max}$) of from 130 ng/ml to 2280 ng/ml, an area under the time/plasma concentration curve from time 0 to 24 hours ($AUC_{0-24h}$) from 2130 ng/ml to 35630 ng/ml.

In another embodiment, the present invention relates to provide an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits the pharmacokinetic characteristic of average minimum drug concentration in plasma at steady state ($C_{min-avg}$) of about 150 ng/ml to 400 ng/ml for a mean duration of about 24 hours.

In another embodiment, the present invention relates to provide an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits the pharmacokinetic characteristic of average maximum drug concentration in plasma at steady state ($C_{max}$-avg) of about 550 ng/ml to 750 ng/ml for a mean duration of about 24 hours.

In another embodiment, the present invention relates to provide an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits the pharmacokinetic characteristic of an average area under the time/plasma concentration curve at steady state from time 0 to 24 hours ($AUC_{0-24h,avg}$) is of about 8000 to 12000 ng·h/ml.

In another embodiment, the present invention relates to an extended release pharmaceutical composition of Clozapine, wherein the pharmaceutical composition lacks a significant food effect on oral administration.

In another embodiment, the present invention relates to an extended release pharmaceutical composition of Clozapine, wherein the difference of $C_{max\text{-}avg}$ and $T_{max}$ at steady state for the pharmaceutical composition in fed state as compared to $C_{max\text{-}avg}$ and $T_{max}$ at steady state for the pharmaceutical composition in fasted state is less than 20%.

Definitions

Unless otherwise indicated, terms in this specification are intended to have their ordinary meaning in the relevant art. Other more specific definitions for certain terms as used in the present application are as set forth below and are intended to apply uniformly throughout the specification and claims unless an otherwise expressly set out definition provides a broader definition.

The term "extended release pharmaceutical composition" as used herein before and throughout the description refers to drug delivery system releasing Clozapine at a predetermined rate, locally or systemically, for a specified period of time. Extended release can be used interchangeably with prolonged release, programmed release, timed release, sustained release, controlled release, and modified release, slow release and other such dosage forms. The present invention relates to extended release pharmaceutical composition of Clozapine, wherein the pharmaceutical composition is in the form of granules, pellets, beads, spheroids or the likes thereof, and the pharmaceutical composition is dispensed or compressed in the form of tablets or mini-tablets, or filled in capsules to provide pharmaceutical composition of Clozapine for oral administration.

The term "Clozapine" used throughout the specification refers to not only Clozapine free base, but also its pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs and pharmaceutically acceptable prodrugs thereof.

The term "reservoir type dosage form" means the composition, wherein water-insoluble polymeric material encloses the drug core.

The term "$C_{min}$" refers to the minimum plasma concentration of Clozapine in the blood after administration of extended release composition. It is the lowest concentration that a drug reaches before the second dose is administered.

The term "$C_{max}$" refers to the peak plasma concentration of Clozapine in the blood following an oral single-dose administration of extended release composition of Clozapine. The $C_{max\text{-}avg}$ is the average or mean value calculated for $C_{max}$ obtained following the oral administration of extended release composition of Clozapine across a group of multiple subjects.

The term "$T_{max}$" refers to the time in hours when $C_{max}$ is achieved following an oral single-dose administration of extended release composition of Clozapine.

The term "AUC" refers to the area under the time/plasma concentration curve following an oral single-dose administration of extended release composition of Clozapine. The area under the plasma concentration versus time curve is expressed from time zero to 24 hours quantifiable concentration ($AUC_{0\text{-}24h}$) and to infinity ($AUC_{0\text{-}infinity}$). The $AUC_{0\text{-}t}$ denotes the area under the plasma concentration versus time curve from time 0 to time t.

The term "half-life" refers to the time required for the drug concentration to reach half of its pharmacological activity.

The "fasted state" or "fasting condition" means the condition, wherein the pharmacokinetic parameters have been measured when the composition of Clozapine is administered orally to a human subject without food. For the fasting condition, following an overnight fast of at least 10 hours, subjects should be administered the drug product with 240 mL (8 fluid ounces) of water. No food should be allowed for at least 4 hours post-dose. Water can be allowed as desired except for one hour before and after drug administration. Subjects should receive standardized meals scheduled at the same time in each period of the study.

The "fed state" or "fed condition" means the condition, wherein there is presence of food in the stomach of the subject such that the absorption of Clozapine drug from the composition can be affected as compared with when there is no food present in the stomach. In some embodiments, a fed state is the state of the subject during the time from the start of food consumption to about 2 hours after food consumption, such as about 30 minutes after food consumption, about 1 hour after food consumption, about 1.5 hours after food consumption, or about 2 hours after food consumption. As used herein, food consumption refers to consuming a substantial amount of food, such as at least one third of a normal meal of a subject, either by volume or by total number of calories consumed.

The bioavailability of orally administered drugs is frequently affected by food-drug interactions. The food effect caused by any interactions of food with drug shall result into change of bioavailability, on-set of therapeutic action, duration of therapeutic effect and incidence of side effects. For the purpose of the present invention, the "food effect" means the condition, wherein the pharmacokinetics parameters of an orally administered extended release pharmaceutical composition of Clozapine are measured and the difference of $C_{max\text{-}avg}$ and $T_{max}$ at steady state for the pharmaceutical composition in fed state as compared to $C_{max\text{-}avg}$ and $T_{max}$ at steady state for the pharmaceutical composition in fasted state is less than 20%.

The term "pharmaceutical composition" means multiparticulates in the form of granules, pellets, beads, spheroids or likes thereof, which is dispensed or compressed in the form of tablets or mini-tablets or filled in capsules to provide extended release oral composition of Clozapine for once daily administration.

The term "seal coat" is synonymous to various terms like separating layer, seal coating layer, intermediate layer, barrier coating layer, film coating and the like. The seal coat comprises a water-soluble substance or water-insoluble substance and one or more pharmaceutically acceptable excipient(s). Preferably, the seal coat comprises hydrophilic polymer. Preferably, the hydrophilic polymer is hydroxypropyl methylcellulose (HPMC or Hypromellose).

The term "acidic coat" mainly comprises an acidic substance, which helps in providing an acidic pH micro-environment between the upper part of the small intestine and the lower part of the large intestine. The acidic pH microenvironment improves solubility and bioavailability of Clozapine.

The term "extended release coat" mainly comprises of extended release polymers and optionally other pharmaceutically acceptable excipients; wherein the extended release coat prolongs the release of Clozapine. Specifically the extended release coat comprises a water insoluble polymer and a water soluble polymer, wherein the water soluble polymer act as pore former and/or a plasticizer.

Suitable "polymers" may include water soluble and water insoluble polymers for the seal coat and/or the extended release coat. Suitable polymers may include one or more of cellulosic polymers/copolymers or its derivatives including methyl cellulose, hydroxypropyl methylcellulose (HPMC or Hypromellose), hydroxyethyl cellulose, hydroxypropyl cellulose, hydroxyethyl methylcellulose, carboxymethylcellulose, sodium carboxymethylcellulose, polyethylene glycol, PEG 400, polyethylene oxides, chitosan, gums, starch derivatives, polyurethanes, polysaccharides, polyalcohols, cellulose derivatives as ethyl cellulose, ethyl cellulose aqueous dispersion, cellulose acetate, poly (alkyl) methacrylate, copolymers of acrylic or methacrylic acid esters, eudragit, polymethacrylates containing quaternary ammonium group, high molecular weight polyvinyl alcohols, polyvinyl acetate dispersion (e.g., Kollidon), waxes, hydrogenated vegetable oil, fatty acids, long chain fatty alcohols, cellulose acetate butyrate or mixtures thereof and other materials known to one of ordinary skill in the art.

Preferably, the water insoluble polymer used in extended release coating is cellulose derivative such as ethyl cellulose and like thereof.

Suitable "plasticizer" may include, but not limited to glycerin, polyethylene glycol, PEG 400, polyethylene glycol monomethyl ether, propylene glycol, sorbitol sorbitan solution or mixtures and like thereof.

Suitable "osmotic agent" may include, but not limited to polyethylene glycol, sucrose, glucose, fructose, sodium chloride, magnesium chloride, potassium nitrate or mixtures and like thereof.

Pharmaceutically acceptable excipient(s) include but are not limited to binders, fillers or diluents, lubricants, osmotic agent, plasticizer, glidants or solvent(s) and mixtures thereof. One excipient can perform more than one function. The excipients may be selected from but are not limited to, starches such as potato starch, wheat starch, corn starch; microcrystalline cellulose, celluloses such as hydroxypropyl cellulose, hydroxyethyl cellulose, hydroxypropyl methyl cellulose (HPMC or Hypromellose), ethyl cellulose, sodium carboxy methyl cellulose; polyethylene oxide, polyvinyl pyrrolidone, poly-N-vinyl amide, polyethylene glycol, gelatin, poly propylene glycol, carbohydrates, confectioner's sugar, compressible sugar, dextrates, dextrin, dextrose, fructose, lactitol, mannitol, sucrose, lactose, calcium phosphate dibasic or tribasic, calcium sulphate, magnesium stearate, aluminum stearate or calcium stearate or zinc stearate, glyceryl behenate, mineral oil, sodium stearyl fumarate, stearic acid, talc, silicon dioxide, magnesium trisilicate, powdered cellulose, talc, tribasic calcium phosphate, calcium silicate, magnesium silicate, colloidal silicon dioxide, croscarmellose sodium, povidone, guar gum, magnesium aluminium silicate, sodium alginate, sodium starch glycolate and other materials known to one of the ordinary skill in the art and combinations thereof.

The solvents that can be used in the present invention include all the solvents well known in the art or their mixtures thereof. In some embodiments, the solvents are selected from the group comprising isopropanol, methylene chloride, acetonitrile, purified water or mixtures thereof.

In another embodiment, the present invention relates to an extended release pharmaceutical composition of Clozapine in the form of multiparticulates like granules, pellets, beads or spheroids comprising:
a) granules, pellets, beads or spheroids comprising Clozapine,
b) optional seal coating with hydrophilic polymer,
c) acidic coating with acidic substance, and/or
d) extended release coating with a water insoluble polymer and a water soluble polymer.

In another embodiment, the present invention relates to a process for preparation of an extended release pharmaceutical composition of Clozapine in the form of multiparticulates such as, for example, granules, pellets, beads, spheroids comprising:
a) Granules, pellets, beads or spheroids comprising Clozapine,
b) Seal coating with hydrophilic polymer,
c) Acidic coating with acidic substance, and/or
d) Extended release coating with a water insoluble polymer and a water soluble polymer.

In a preferred embodiment, the stable extended release pharmaceutical composition comprises multiparticulates in the form of pellets that comprise:
(i) a core containing Clozapine with pharmaceutically acceptable excipients,
(ii) a first seal coat layer comprising a hydrophilic polymer,
(iii) an acidic coat layer with acidic substance,
(iv) a second seal coat layer comprising a hydrophilic polymer,
(v) an extended release coat with a water insoluble polymer and a water soluble polymer, and/or
(vi) a third seal coat layer comprising a hydrophilic polymer.

In another embodiment, the extended release coating composition of Clozapine contains ethyl cellulose and polyethylene glycol 400. The coating composition comprises polyethylene glycol 400 (PEG-400) as water soluble pore former. Polyethylene glycol 400 is in liquid state at room temperature and hygroscopic in nature. Due to this property, Clozapine pellets become cohesive during manufacturing operations and storage. This cohesive nature affects free flow of pellets during operations. To reduce the cohesive nature of PEG-400 in extended release film, hypromellose seal coat is applied over extended release coat.

In another embodiment, the present invention relates to a process for the preparation of extended release pharmaceutical composition of Clozapine in the form of multiparticulates like granules, pellets, beads or spheroids.

In another embodiment the present invention relates to an extended release pharmaceutical composition of Clozapine, wherein release of Clozapine from the composition is extended up to 24 hours.

In another embodiment, the present invention relates to an extended release pharmaceutical composition of Clozapine, wherein the pharmaceutical composition is a reservoir type dosage form, and when dosed to a patient once daily achieves at steady state, $AUC_{0-24h}$, $C_{max}$ and $C_{min}$ in the patient's plasma that are within 80 to 125% bioequivalence criteria compared to immediate release Clozapine dosed at the same total daily dose divided twice per day.

In another embodiment, the present invention relates to a method for maintaining a therapeutically effective concentration of Clozapine to reduce side effect and reduce patient burden to take multiple pills, wherein the method comprises administering to the patient, about 12.5 mg to about 400 mg of Clozapine once daily in an extended release pharmaceutical composition.

In another embodiment, the present invention relates to an extended release pharmaceutical composition of Clozapine, wherein the pharmaceutical composition is a reservoir type dosage form, and when dosed to a patient once daily achieves at steady state, $AUC_{0-24h}$, $C_{max}$ and $C_{min}$ compared to immediate release Clozapine dosed at the same total daily dose divided twice per day.

In another embodiment, the present invention relates to an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day.

In another embodiment, the present invention relates to an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits the pharmacokinetic characteristic of a minimum drug concentration in plasma ($C_{min}$) from 20 ng/ml to 1070 ng/ml.

In another embodiment, the present invention relates to an extended release pharmaceutical composition of Clozapine, wherein the pharmaceutical composition is a reservoir type dosage form containing 200 mg of Clozapine, and when dosed to a patient once daily achieves at steady state, an $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits the pharmacokinetic characteristic of a maximum drug concentration in plasma ($C_{max}$) from 130 ng/ml to 2280 ng/ml.

In another embodiment, the present invention relates to an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits the pharmacokinetic characteristic of an area under the time/plasma concentration curve from time 0 to 24 hours ($AUC_{0-24h}$) is from 2130 ng/ml to 35630 ng/ml.

In another embodiment, the present invention relates to an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits the pharmacokinetic characteristic of a minimum drug concentration in plasma ($C_{min}$) from 20 ng/ml to 1070 ng/ml, a maximum drug concentration in plasma ($C_{max}$) from 130 ng/ml to 2280 ng/ml, an area under the time/plasma concentration curve from time 0 to 24 hours $AUC_{0-24h}$ is from 2130 ng/ml to 35630 ng/ml.

In another embodiment, the present invention relates to an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits the pharmacokinetic characteristic of average minimum drug concentration in plasma at steady state ($C_{min-avg}$) from about 150 ng/ml to 400 ng/ml for a mean duration of about 24 hours.

In another embodiment, the present invention relates to an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits the pharmacokinetic characteristic of average maximum drug concentration in plasma ($C_{max-avg}$) from about 550 ng/ml to 750 ng/ml for a mean duration of about 24 hours.

In another embodiment, the present invention relates to an extended release pharmaceutical composition of Clozapine, wherein the pharmaceutical composition is a reservoir type dosage form containing 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg of immediate release Clozapine dosed twice a day, wherein the pharmaceutical composition exhibits the pharmacokinetic characteristic of an average area under the time/plasma concentration curve at steady state from time 0 to 24 hours ($AUC_{0-24h, avg}$) is of about 8000 to 12000 ng·h/ml.

The pharmacokinetic parameters obtained after a single dose of 200 mg of extended release composition of Clozapine is bioequivalent to 100 mg immediate release tablets administered twice a day under fasting conditions. The composition of the present invention can be used for treatment of schizophrenia patients, thereby reducing the risk of recurrent suicidal behavior in patients with schizophrenia or schizoaffective disorder and Parkinson-related psychosis.

In another embodiment, the present invention relates to an extended release pharmaceutical composition of Clozapine, wherein the difference of $C_{max-avg}$ and $T_{max}$ at steady state for the pharmaceutical composition in fed state as compared to $C_{max-avg}$ and $T_{max}$ at steady state for the pharmaceutical composition in fasted state is less than 20%. In a preferred embodiment, the present invention relates to an extended release pharmaceutical composition of Clozapine, wherein the difference of $C_{max-avg}$ and $T_{max}$ at steady state for the pharmaceutical composition in fed state as compared to $C_{max-avg}$ and $T_{max}$ at steady state for the pharmaceutical composition in fasted state is less than 10%; more specifically less than 5%.

The pharmacokinetics results for Clozapine 50 mg/ml suspension and Clozaril® 100 mg tablets available from Biopharmaceutics review are as described below in Table 1.

TABLE 1

| Pharmacokinetics, fed and fasting. | | |
|---|---|---|
| Pharmacokinetic Parameters | Clozapine 50 mg/ml Suspension | Clozaril ® 100 mg tablets |
| Fasting Pharmacokinetic Results: | | |
| Cmax-avg (ng/ml) | 275 | 275 |
| Tmax (hr) | 2.18 | 2.53 |
| Fed Pharmacokinetic Results: | | |

TABLE 1-continued

Pharmacokinetics, fed and fasting.

| Pharmacokinetic Parameters | Clozapine 50 mg/ml Suspension | Clozaril® 100 mg tablets |
|---|---|---|
| Cmax-avg (ng/ml) | 220 | 220 |
| Tmax (hr) | 3.12 | 4.94 |

From the above pharmacokinetic results for Clozapine 50 mg/ml Suspension, it is apparent that the difference of $C_{max-avg}$ and $T_{max}$ at steady state for Clozapine Suspension in fed state as compared to $C_{max-avg}$ and $T_{max}$ at steady state for Clozapine Suspension in fasted state is more than 20%. Therefore, there is a significant food effect in Clozapine 50 mg/ml Suspension dosage form.

From the above pharmacokinetic results for Clozaril® 100 mg tablets, it is apparent that the difference of $C_{max}$-avg and $T_{max}$ at steady state for Clozaril tablets in fed state as compared to $C_{max-avg}$ and $T_{max}$ at steady state for Clozaril tablets in fasted state is more than 20%. Therefore, there is a significant food effect in Clozaril® 100 mg tablet dosage form.

The food effect study for extended release composition of Clozapine and the obtained statistical results are as described below. Study Title: A multicentric, open label, balanced, randomized, two-period, two-sequence, crossover, steady state, food effect study of Clozapine extended release capsule 200 mg once daily (Test drug, according to the present invention) after multiple dose administration in schizophrenic patients under fasted and fed conditions.

Study Design: A multicentric, open label, balanced, randomized, two-period, two-20 sequence, crossover, steady state, food effect study of Clozapine extended release capsule 200 mg once daily (Test drug, according to the present invention) after multiple dose administration in adult schizophrenic patients under fasting and fed conditions. Washout period: No wash-out was given between Period-I and Period-II. Number of patients enrolled: 87 Patients. (See, Table 2).

TABLE 2

Summary for pharmacokinetic parameters of Clozapine

| | Tmax, ss (hrs) | Cmax, ss (ng · h/ml) |
|---|---|---|
| Test Formulation-T2 (under fed condition) | | |
| N | 87 | 87 |
| Mean/Average | 4.48 | 630.37 |
| Geometric Mean | 4.39 | 560.22 |
| Test Formulation-T1 (under fasting condition) | | |
| N | 87 | 87 |
| Mean/Average | 4.63 | 645.20 |
| Geometric Mean | 4.36 | 569.58 |

The results of the food effect study of Clozapine extended release composition shows that the difference of $C_{max-avg}$ and $T_{max}$ at steady state for the pharmaceutical composition in fed state is less than 5% as compared to $C_{max-avg}$ and $T_{max}$ at steady state for the pharmaceutical composition in fasted state. Therefore, the extended release pharmaceutical composition of the present invention lacks significant food effect on oral administration.

Hereinafter the process of manufacturing the pharmaceutical composition of the present invention is explained in detail:

EXAMPLES

The following examples are illustrative of the present invention, and the examples should not be considered as limiting the scope of this invention in any way, as these examples and other equivalents thereof will become apparent to those versed in the art, in the light of the present disclosure.

Example 1: Extended Release Pharmaceutical Composition of Clozapine

This example demonstrates that 12.5, 25, 50, 100 and 200 mg strengths of compositions in accordance with embodiments of the disclosure are dose proportional.

TABLE 3

Composition ingredients & relative amounts

| Ingredients | Amount (%) |
|---|---|
| Clozapine USP | 20-40 |
| Diluent | 5-35 |
| Binder | 2-10 |
| Seal Coating | 2-20 |
| Acidic Coating | 20-40 |
| Extended release coating | 2-20 |
| Glidant | 0.2-2 |

The Clozapine composition is manufactured by a process as described herein and can be modified using other process steps and equipment generally known in the art. Generally, the process can include a methodology as follows. Sift Clozapine with other excipients through a screen or mesh. Prepare a binder solution. Granulate the dry blend with binder solution. Subsequently apply seal coating solution, acidic coating solution and extended release solution on extrudes or spheroids or granules by using suitable coating equipment. Blend the coated extrudes or spheroids or granules with a suitable glidant.

Example 2: Extended Release Pharmaceutical Composition of Clozapine

TABLE 4

Extended release composition.

| | Theoretical Quantity mg/Capsules | | | | |
|---|---|---|---|---|---|
| Ingredients | 12.5 | 25 | 50 | 100 | 200 |
| Granulation or Extrusion Spheronization | | | | | |
| Clozapine USP | 12.5 | 25 | 50 | 100 | 200 |
| Microcrystalline Cellulose | 5.375 | 10.75 | 21.5 | 43 | 86 |
| Polyglycol 4000PF (PEG 4000) | 2.125 | 4.25 | 8.5 | 17 | 34 |
| First Seal Coating | | | | | |
| Hypromellose E5 | 1.00 | 2.00 | 4.00 | 8.00 | 16.00 |
| Purified water | q.s. | q.s. | q.s. | q.s. | q.s. |
| Acidic Coating | | | | | |
| Tartaric Acid | 9.375 | 18.75 | 37.5 | 75 | 150 |

TABLE 4-continued

Extended release composition.

| Ingredients | Theoretical Quantity mg/Capsules | | | | |
|---|---|---|---|---|---|
| | 12.5 | 25 | 50 | 100 | 200 |
| Sodium Chloride | 3.125 | 6.25 | 12.5 | 25 | 50 |
| Purified Water | q.s. | q.s. | q.s. | q.s. | q.s. |
| Second Seal Coating | | | | | |
| Hypromellose E5 | 1.00 | 2.00 | 4.00 | 8.00 | 16.00 |
| Isopropyl alcohol | q.s. | q.s. | q.s. | q.s. | q.s. |
| Dichloromethane | q.s. | q.s. | q.s. | q.s. | q.s. |
| Extended release coating | | | | | |
| Ethyl Cellulose 10 cps | 2.07 | 4.14 | 8.28 | 16.56 | 33.12 |
| PEG 400 | 0.69 | 1.38 | 2.76 | 5.52 | 11.04 |
| Isopropyl alcohol | q.s. | q.s. | q.s. | q.s. | q.s. |
| Dichloromethane | q.s. | q.s. | q.s. | q.s. | q.s. |
| Third Seal Coating | | | | | |
| Hypromellose E5 | 1.125 | 2.25 | 4.5 | 9.00 | 18.00 |
| Isopropyl alcohol | q.s. | q.s. | q.s. | q.s. | q.s. |
| Dichloromethane | q.s. | q.s. | q.s. | q.s. | q.s. |
| Blending | | | | | |
| Talc | 0.365 | 0.73 | 1.46 | 2.92 | 5.84 |
| Cellulose Capsules | Size 4 | Size 4 | Size 3 | Size 1 | Size 00 |
| Theoretical Net Content | 38.75 | 77.50 | 155.00 | 310.00 | 620.00 |

The manufacturing process is described as an illustrative embodiment in accordance with the disclosure. Generally, the process can include a methodology as follows. Co-sift Clozapine and microcrystalline cellulose through a sieve (screen or mesh). Granulate the dry blend material with PEG solution in a granulator, or prepare the pellets or spheroids using a spheronizer. Dry the pellets in a suitable processor to apply first seal coating layer in a suitable coating instrument. Apply acidic coat on the seal coated pellets, followed by the second seal coating on the obtained pellets in a suitable coating instrument. Subsequently apply the extended release coating on the obtained seal-coated pellets, followed by the third seal coating on the extended release coated pellets in a suitable coating instrument. Blend seal coated pellets with a suitable glidant. Fill the lubricated pellets in the capsules according to fill weight of each strength.

Example 3: Clozapine Pivotal Bioequivalence Study

Study Title: A multi-centric open label, balanced, randomized, two treatment, two-period, two-sequence, crossover, steady state, comparative bioavailability Study of Clozapine extended release capsule 200 mg once daily (Test drug, in accordance with the example embodiments illustrated in Table 4) with Clozaril® tablets 100 mg twice daily (Reference Drug, Novartis pharmaceuticals corporation, USA) after multiple dose administration in adult schizophrenic patients under fasting conditions (see, Table 5).

TABLE 5

Comparison of composition with listed drug product

| Test Product | Listed Drug Product |
|---|---|
| Investigational Product: Clozapine extended release capsules (disclosed herein) | Investigational Product: Clozaril ® tablets of Novartis Pharmaceuticals Corporation, USA. |
| Active ingredient: Clozapine | Active ingredient: Clozapine |
| Dosage: 200 mg once daily | Dosage: 100 mg twice daily |
| Manufacturer: Intas Pharmaceuticals Limited, India. | Manufacturer: Novartis Pharmaceuticals Corporation, USA. |
| Pharmaceutical form: Extended release capsule | Pharmaceutical form: Immediate release tablet |
| Route of administration: Per oral | Route of administration: Per oral |
| Storage: Temperature should not exceed 30° C. (86° F.). | Storage: Temperature should not exceed 30° C. (86° F.). |

Study Design: An open label, balanced, randomized, two-treatment, two-period, two-sequence, crossover, multi-centric comparative bioavailability study of two formulations of Clozapine (Extended Release Formulation of 200 mg versus immediate Release Formulation of 2×100 mg) under fasting conditions after multiple dose administration at steady state in adult schizophrenic patients stabilized on Clozapine 200 mg per day.

Washout period: No wash-out was given between Period-I and Period-II

Number of Patients Enrolled: 136 Patients

Study Results: Extended Release, 200 mg once daily in accordance with the Examples above (Test drug) vs Immediate Release Clozaril® tablets 100 mg twice daily (Listed drug, Novartis Pharmaceuticals Corporation, USA). See Table 6.

TABLE 6

Pharmacokinetic profiles

| Description | $C_{max, ss}$ (ng/ml) | | $C_{min, ss}$ (ng/ml) | | $AUC_{0-24, ss}$ (ng · h/ml) | |
|---|---|---|---|---|---|---|
| | Test | Listed Drug | Test | Listed Drug | Test | Listed Drug |
| N | 132 | 132 | 132 | 132 | 132 | 130 |
| Geometric Least square Mean | 558.73 | 621.75 | 211.14 | 254.05 | 8132.39 | 9360.17 |
| Geometric Mean | 573.95 | 635.84 | 291.82 | 264.86 | 8405.37 | 9615.42 |
| Average | 650.47 | 709.18 | 281.66 | 323.34 | 9877.47 | 11120.29 |
| Minimum | 137.82 | 119.09 | 23.61 | 0.000 | 2149.17 | 1914.75 |
| Maximum | 2267.20 | 2278.40 | 1060.23 | 1426.10 | 35608.98 | 42257.72 |

TABLE 6-continued

Pharmacokinetic profiles

| | $C_{max, ss}$ (ng/ml) | | $C_{min, ss}$ (ng/ml) | | $AUC_{0-24, ss}$ (ng · h/ml) | |
|---|---|---|---|---|---|---|
| Description | Test | Listed Drug | Test | Listed Drug | Test | Listed Drug |
| % T/R | | 89.9 | | 83.1 | | 86.9 |

The pharmacokinetic parameters obtained for 200 mg of extended release composition of Clozapine is desirable as it provides a once-daily dosage form that is bioequivalent to 100 mg immediate release tablets administered twice a day and is expected to improve patient compliance relative to forms requiring multiple daily dosages.

We claim:

1. An extended release oral pharmaceutical composition of 12.5 mg to 200 mg of Clozapine, wherein the pharmaceutical composition is a reservoir type dosage form, and when dosed to a patient once daily achieves at steady state, $AUC_{0-24h}$, $C_{max}$ and $C_{min}$ in the patient's plasma that are within 80 to 125% bioequivalence criteria compared to immediate release Clozapine dosed at the same total daily dose divided twice per day, wherein the said composition comprises: a) granules, pellets, beads or spheroids comprising Clozapine with pharmaceutically acceptable excipients, b) a first seal coat layer comprising a hydrophilic polymer, c) an acidic coating with acidic substance, d) a second seal coat layer comprising a hydrophilic polymer, (e) an extended release coating with a water insoluble polymer and a water soluble polymer and (f) a third seal coat layer comprising a hydrophilic polymer, wherein, the amount of the seal coating in the composition is from 2-20%;

the amount of the acidic coating in the composition is from 20-40%;

the amount of extended release coating in the composition is from 2-20%; and wherein the hydrophilic polymer comprises hydroxypropyl methylcellulose, HPMC, Hypromellose, hydroxyethyl cellulose, hydroxypropyl cellulose, hydroxyethyl methylcellulose, carboxymethylcellulose, polyethylene glycol, polyethylene oxides, or polyalcohols;

the water insoluble polymer comprises Chitosan, polyurethanes, ethyl cellulose, cellulose acetate or waxes; and the water soluble polymer comprises hydroxypropyl methylcellulose, HPMC, Hypromellose, hydroxyethyl cellulose, hydroxypropyl cellulose, hydroxyethyl methylcellulose, carboxymethylcellulose, polyethylene glycol, polyethylene oxides or polyalcohols.

2. The extended release oral pharmaceutical composition of Clozapine as claimed in claim 1, wherein the pharmaceutical composition comprises 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg immediate release Clozapine dosed at the same total daily dose divided twice per day.

3. The extended release oral pharmaceutical composition of Clozapine as claimed in claim 1, wherein the pharmaceutical composition comprises 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg immediate release Clozapine dosed at the same total daily dose divided twice per day; wherein the pharmaceutical composition provides a minimum drug concentration in plasma at steady state ($C_{min}$) from 20 ng/ml to 1070 ng/ml.

4. The extended release oral pharmaceutical composition of Clozapine as claimed in claim 1, wherein the pharmaceutical composition comprises 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg immediate release Clozapine dosed at the same total daily dose divided twice per day; wherein the pharmaceutical composition provides a maximum drug concentration in plasma at steady state ($C_{max}$) from 130 ng/ml to 2280 ng/ml.

5. The extended release oral pharmaceutical composition of Clozapine as claimed in claim 1, wherein the pharmaceutical composition comprises 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg immediate release Clozapine dosed at the same total daily dose divided twice per day; wherein the pharmaceutical composition provides an area under the time/plasma concentration curve from time 0 to 24 hours at steady state ($AUC_{0-24h}$) from 2130 ng/ml to 35630 ng/ml.

6. The extended release oral pharmaceutical composition of Clozapine as claimed in claim 1, wherein the pharmaceutical composition comprises 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg immediate release Clozapine dosed at the same total daily dose divided twice per day; wherein the pharmaceutical composition provides a minimum drug concentration in plasma at steady state ($C_{min}$) of from 20 ng/ml to 1070 ng/ml, a maximum drug concentration in plasma at steady state ($C_{max}$) of from 130 ng/ml to 2280 ng/ml, and an area under the time/plasma concentration curve from time 0 to 24 hours at steady state ($AUC_{0-24h}$) from 2130 ng/ml to 35630 ng/ml.

7. The extended oral release oral pharmaceutical composition of Clozapine as claimed in claim 1, wherein the pharmaceutical composition comprises 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg immediate release Clozapine dosed at the same total daily dose divided twice per day; wherein the pharmaceutical composition provides an average minimum drug concentration in plasma at steady state ($C_{min-avg}$) from about 150 ng/ml to 400 ng/ml for a mean duration of about 24 hours.

8. The extended release oral pharmaceutical composition of Clozapine as claimed in claim 1, wherein the pharmaceutical composition comprises 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg immediate release Clozapine dosed at the same total daily dose divided twice per day; wherein the pharmaceutical composition provides an average maximum drug concentration in plasma at steady state ($C_{max-avg}$) from about 550 ng/ml to 750 ng/ml for a mean duration of about 24 hours.

9. The extended release oral pharmaceutical composition of Clozapine as claimed in claim 1, wherein the pharmaceutical composition comprises 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg immediate release Clozapine dosed at the same total daily dose divided twice per day; wherein the pharmaceutical composition provides an average area under the time/plasma concentration curve at steady state from time 0 to 24 hours ($AUC_{0-24h,avg}$) from about 8000 to 12000 ng·h/ml.

10. The extended release oral pharmaceutical composition of Clozapine as claimed in claim 1, wherein the pharmaceutical composition comprises 200 mg of Clozapine, and when dosed to a patient once daily achieves at steady state, $AUC_{0-24h}$, $C_{max}$ and $C_{min}$ in the patient's plasma that are within 80 to 125% bioequivalence criteria compared to 100 mg immediate release Clozapine dosed at the same total daily dose divided twice per day; wherein the pharmaceutical composition provides an average minimum drug concentration in plasma at steady state ($C_{min-avg}$) from about 150 ng/ml to 400 ng/ml for a mean duration of about 24 hours, average maximum drug concentration in plasma at steady state ($C_{max-avg}$) from about 550 ng/ml to 750 ng/ml for a mean duration of about 24 hours, and average area under the time/plasma concentration curve at steady state from time 0 to 24 hours ($AUC_{0-24h,avg}$) from about 8000 to 12000 ng·h/ml.

11. The extended release oral pharmaceutical composition of Clozapine as claimed in claim 1, wherein the pharmaceutical composition is dispensed or compressed in the form of tablets or mini-tablets, or filled in capsules to provide pharmaceutical composition of Clozapine for oral administration.

* * * * *

UNITED STATES PATENT AND TRADEMARK OFFICE
CERTIFICATE OF CORRECTION

| | |
|---|---|
| PATENT NO. | : 11,648,207 B1 |
| APPLICATION NO. | : 17/716790 |
| DATED | : May 16, 2023 |
| INVENTOR(S) | : Rikin Patel et al. |

It is certified that error appears in the above-identified patent and that said Letters Patent is hereby corrected as shown below:

In the Specification

Column 15-17 Table 6, the value in row Geometric Mean, column Cmin,ss (ng/ml) - Test. This value should read as 219.82 as shown below:

| Description | $C_{max,ss}$ (ng/ml) | | $C_{min,ss}$ (ng/ml) | | $AUC_{0-24,ss}$ (ng.h/ml) | |
|---|---|---|---|---|---|---|
| | Test | Listed Drug | Test | Listed Drug | Test | Listed Drug |
| N | 132 | 132 | 132 | 132 | 132 | 130 |
| Geometric Least square Mean | 558.73 | 621.75 | 211.14 | 254.05 | 8132.39 | 9360.17 |
| Geometric Mean | 573.95 | 635.84 | 219.82 | 264.86 | 8405.37 | 9615.42 |
| Average | 650.47 | 709.18 | 281.66 | 323.34 | 9877.47 | 11120.29 |
| Minimum | 137.82 | 119.09 | 23.61 | 0.000 | 2149.17 | 1914.75 |
| Maximum | 2267.20 | 2278.40 | 1060.23 | 1426.10 | 35608.98 | 42257.72 |
| % T/R | 89.9 | | 83.1 | | 86.9 | |

Signed and Sealed this
Twelfth Day of November, 2024

Katherine Kelly Vidal
*Director of the United States Patent and Trademark Office*